US006184206B1

(12) United States Patent
Smith et al.

(10) Patent No.: US 6,184,206 B1
(45) Date of Patent: Feb. 6, 2001

(54) INTEGRIN LIGAND DISSOCIATORS (75) Inventors: Jeffrey W. Smith, San Diego, CA (US); Dana D. Hu, Maryland Heights, MO (US)

(73) Assignee: The Burnham Institute, La Jolla, CA (US)

( * ) Notice: Under 35 U.S.C. 154(b), the term of this patent shall be extended for 0 days.

(21) Appl. No.: 09/146,503

(22) Filed: Sep. 2, 1998

Related U.S. Application Data (60) Provisional application No. 60/057,463, filed on Sep. 3, 1997.

(51) Int. Cl.$^7$ .......................... A61K 38/00; A61K 35/14; C07K 5/00
(52) U.S. Cl. .................................. 514/14; 514/8; 514/11; 514/12; 514/17; 514/18; 530/300; 530/317; 530/324; 530/327; 530/329; 530/331; 530/380; 530/382; 530/395
(58) Field of Search ................................... 514/14, 8, 11, 514/12, 17, 18; 530/300, 317, 324, 327, 329, 331, 380, 382, 395

(56) References Cited

U.S. PATENT DOCUMENTS

| 4,666,884 | 5/1987 | Hawiger et al. ........................ 514/13 |
| 5,470,738 | * 11/1995 | Frelinger, III et al. ......... 435/240.27 |
| 5,654,267 | 8/1997 | Vuori et al. ............................... 514/2 |
| 5,773,412 | 6/1998 | Cheng et al. ............................ 514/11 |
| 5,792,745 | 8/1998 | Cheng et al. ........................... 514/11 |

OTHER PUBLICATIONS

Mousa et al. "Antiplatelet and Antithrombotic Efficacy of DMP 728, a Novel Platelet GPIIb/IIIa Receptor Antagonist" *Circulation* 89(1):3–12, Jan. 1994.

Phillips et al. "GPIIb–IIIa: The Responsive Integrin" *Cell* 65:359–362, May 3, 1991.

Cook et al. "Nonpeptide Glycoprotein IIb/IIIa Inhibitors. 15. Antithrombotic Efficacy of L–738, 167, a Long–Acting GPIIb/IIIa Antagonist, Correlates with Inhibition of Adenosine Diphosphate–Induced Platelet Aggregation but not with Bleeding Time Prolongation" *J. Pharm. and Experimental Therapeutics*, 281 (2) :677–689, 1997.

Kaida et al. "Antiplatelet Effect of FK633, a Platelet Glycoprotein IIb/IIIa Antagonist, on Thrombus Formation and Vascular Patency after Thrombolysis in the Injured Hamster Cartoid Artery" *Thrombosis and Haemostasis* 77(3):562–567, 1997.

Mousa et al. "Prevention of Carotid Artery Thrombosis by Oral Platelet GPIIb/IIIa Antagonist in Dogs" *Stroke* 28(4):830–836, Apr. 1997.

Frishman et al. "Novel Antiplatelet Therapies for Treatment of Patients with Ischemic Heart Disease:Inhibitors of the Platelet Glycoprotein IIb/IIIa Integrin Receptor" *Am. Heart J.* 130:877–892, Oct., 1995.

(List continued on next page.)

*Primary Examiner*—Christopher S. F. Low
*Assistant Examiner*—Abdel A. Mohamed
(74) *Attorney, Agent, or Firm*—Needle & Rosenberg, P.C.

(57) ABSTRACT

The invention provides a method of disaggregating a ligand:integrin receptor complex. Specifically, the invention provides a method of disaggregating an existing platelet thrombus in a blood vessel in a subject, comprising administering to the subject a compound which dissociates fibrinogen bound to a first site on platelet glycoprotein IIB-IIIa, by binding a second interacting site on the platelet glycoprotein IIB-IIIa, thereby disaggregating the platelet thrombus. The present invention also provides a method of screening compounds for the ability to dissociate a ligand from its integrin receptor by binding an interacting second site, comprising contacting the compound with an existing ligand:integrin receptor complex and determining if the complex dissociates.

9 Claims, 5 Drawing Sheets

OTHER PUBLICATIONS

Smith et al. "Protein Loop Grafting to Construct a Variant of Tissue–type Plasminogen Activator that Binds Platelet Integrin $\alpha_{IIb}\beta_3$" *J. Biol. Chem.* 270(51):30486–30490, Dec. 22, 1995.

Coller et al. "New Antiplatelet Agents: Platelet GPIIb/IIIa Antagonists" *Thrombosis and Haemostasis* 74(1):302–308, 1995.

Smith et al. "Building Synthetic Antibodies as Adhesive Ligands for Integrins"*J. Biol. Chem.* 269(52):32788–32795, 1994.

Smith et al. "A Mechanism for Divalent Cation Regulation of $\beta_3$–Integrins" *J. Biol. Chem.* 269(2):960–967, Jan. 14, 1994.

Smith et al. "Building Synthetic Antibodies as Adhesive Ligand for Integrins" *J. Biol. Chem.* 269(52):32788–32795, Dec., 1994.

Nicholson et al. "SC–49992–A Potent and Specific Inhibitor of Platelet Aggregation" *Thrombosis Research* 74(5):523–535, 1994.

Barbas et al. "High–Affinity Self–Reactive Human Antibodies by Design and Selection: Targeting the Integrin Ligand Binding Site" *Proc. Natl. Acad. Sci. USA* 90:1003–1007, Nov. 1993.

Zablocki et al. "Potent in vitro and in vivo Inhibitors of Platelet Aggregation Based upon the Arg–Gly–Asp–Phe Sequence of Fibrinogen. A Proposal on the Nature of the Binding Interaction between the Arg–Guanidine of RGDX Mimetics and the Platelet GP IIb–IIIa Receptor" *J. Med. Chem.* 36:1811–1819, 1993.

Calvete et al. "Localization of the Cross–Linking sites of RGD and KQAGDV Peptides to the Isolated Fibrinogen Receptor, the Human Platelet Integrin Glicoprotein IIb/IIIa Influence of Peptide Length" *Eur. J. Biochem.* 206:759–765, 1992.

Cheresh, David and Spiro, Robert "Biosynthetic and Functional Properties of an Arg–Gly–Asp–Directed Receptor Involved in Human Melanoma Cell Attachment to Vitronectin, Fibrinogen, and von Willebrand Factor" *J. Biol. Chem.* 262(36):17703–17711, Dec. 1987.

Coller, Barry S. "A New Murine Monoclonal Antibody Reports an Activation–Dependent Change in the Conformation and/or Microenvironment of the Platelet Glycoprotein IIb/IIIa Complex" *J. Clin. Invest.* 76:101–108, Jul. 1985.

Frishman et al., Am. Heart. J. vol. 130, pp. 877–892, Oct. 1995.*

* cited by examiner

INTEGRIN LIGAND DISSOCIATORS

This application claims priority to Provisional Application Ser. No. 60/057,463, which was filed on Sep. 3, 1997.

This invention was made with government support under grants CA 56483 and AR 42750 awarded by the National Institutes of Health. The government has certain rights in the invention.

BACKGROUND OF THE INVENTION

1. Field of the Invention

The present invention is related to the field of dissociating ligands from the receptors to which they bind. In particular, the present invention relates to dissociating ligands from integrins and thus treating diseases or conditions associated with binding of the ligands.

2. Background Art

Anti-platelet compounds are useful in treating many cardiovascular diseases including myocardial infarction, restenosis, unstable angina and possibly even atherosclerosis. One target for anti-platelet drugs is the platelet surface receptor called GPIIb-IIa. GPIIb-IIIa is an $\alpha\beta$ heterodimer present on the platelet surface and is the platelet fibrinogen receptor. At wounds or sites of vascular injury, GPIIb-IIIa mediates platelet adhesion and platelet aggregation. The formation of these platelet thrombi halt blood loss. Unfortunately, platelets can also adhere aberrantly to blood vessel walls, particularly at sites of atherosclerotic plaques. These platelet-rich thrombi can cause unstable angina and when activated, can lead to myocardial infarct.

GPIIb-IIa is a member of the integrin protein family of cell adhesion receptors. GPIIb-IIIa is one of the integrins that can bind to the arg-gly-asp (RGD) peptide motif. This peptide motif is found within a number of adhesive proteins and also in several of the ligands for IIb-IIIa. The primary physiologic ligand for GPIIb-IIIa is fibrinogen, a soluble plasma borne protein that contains two RGD motifs.

There is now great interest in developing small molecule antagonists of IIb-IIIa. Many candidate antagonists of IIb-IIIa have been developed. Most of these are structural mimics of RGD. Current understanding of IIb-IIIa indicates that it contains a single ligand binding pocket which can bind to both RGD and to the gamma chain sequence of fibrinogen. Hence, it is believed that antagonists of IIb-IIIa which bind at this single ligand binding site will be efficacious in preventing the formation of platelet aggregates because they will block the association of fibrinogen with IIb-IIIa.

Figure 2:
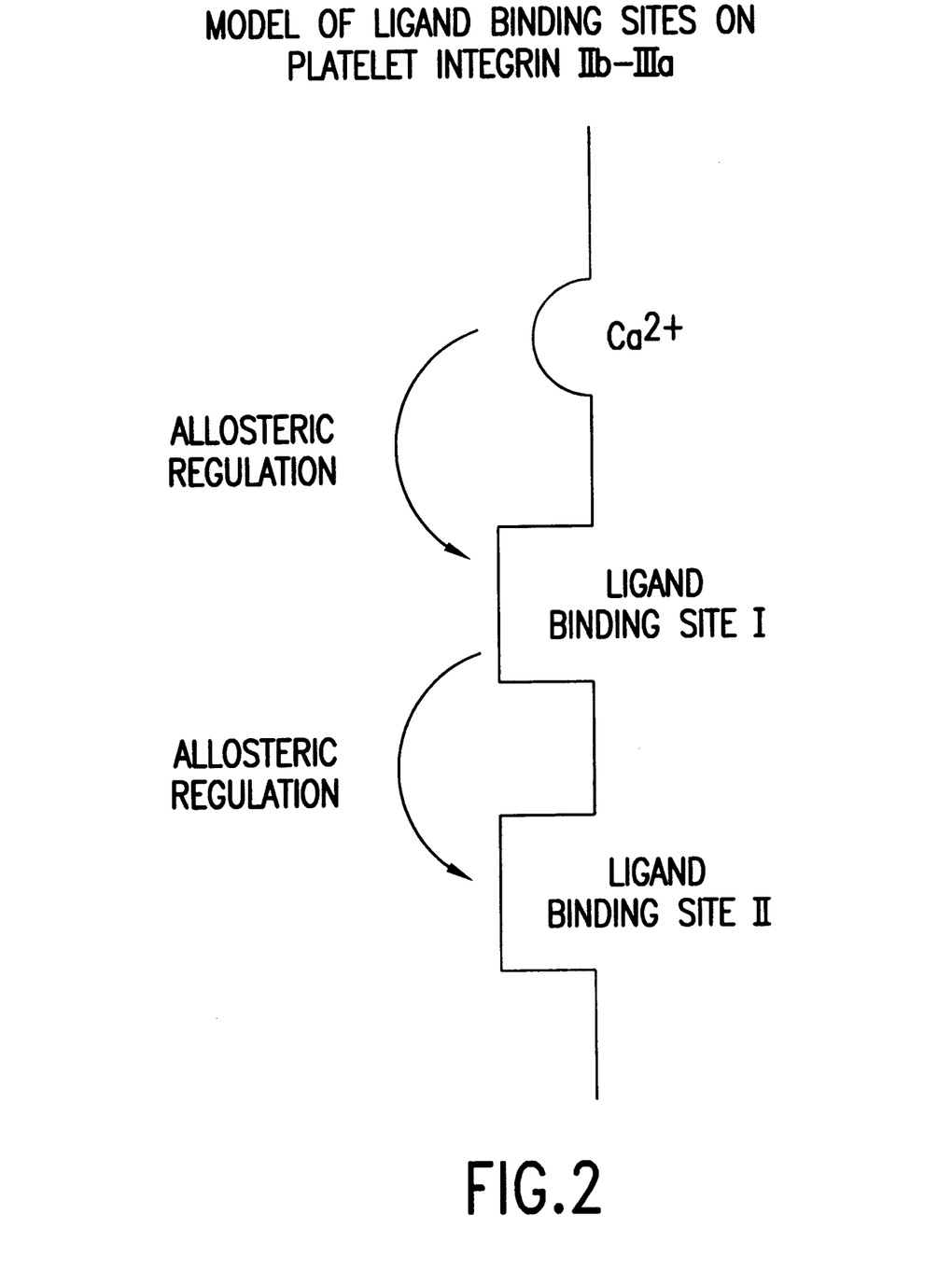
FIG. 2. A proposed model of two interacting ligand binding sites on IIb-IIIa. Ligand Binding Site I interacts with RGD ligands including 52012 and Fab-9. Fibrinogen binds to Ligand Binding Site II.

The present invention provides evidence that IIb-IIIa contains at least two ligand binding pockets and that these two sites are interacting (FIG. 2). The present invention also provides evidence that ligands which bind at Ligand Binding Site I can enact the dissociation of ligand that is already pre-bound at Site II. Because of their unique ability to induce the dissociation of fibrinogen from IIb-IIIa, these antagonists are called Integrin-Ligand Dissociators. Furthermore, the present invention demonstrates that Integrin-Ligand Dissociators are able to enact the dissolution of pre-formed platelet aggregates. These findings indicate a novel approach toward anti-platelet therapy that is a strong departure from the current prophylactic strategy of applying antagonist prior to formation of vascular occlusions. Rather, the present invention demonstrates that the Integrin-Ligand Dissociators of this invention can be applied to reverse platelet aggregates that have already formed.

SUMMARY OF THE INVENTION

The present invention provides a method of disaggregating an existing platelet thrombus in a blood vessel in a subject, comprising administering to the subject a compound which dissociates fibrinogen bound to a first site on platelet glycoprotein IIb-IIIa, by binding a second interacting site on platelet glycoprotein IIb-IIIa, thereby disaggregating the platelet thrombus.

Further provided is a method of screening a compound for the ability to dissociate a ligand from its integrin receptor by binding an interacting second site, comprising contacting the compound with an existing ligand:integrin receptor complex and determining if the complex dissociates.

The present invention additionally provides a method of dissociating a ligand bound to a first site on an integrin receptor, comprising contacting a ligand:integrin receptor complex with a molecule capable of binding a second interacting site on the integrin receptor, thereby dissociating the ligand bound to a first site on the integrin receptor.

Various other objectives and advantages of the present invention will become apparent from the following detailed description.

BRIEF DESCRIPTION OF THE DRAWINGS

FIGS. 3A and 3B. RGD Ligands dissociate fibrinogen from IIb-IIIa. Studies were conducted to determine if RGD ligands like Fab-9 and 52012 can dissociate fibrinogen that is pre-bound to IIb-IIIa. FIG. 3A: $^{125}$I-fibrinogen was allowed to bind to purified IIb-IIIa, and free ligand was removed by washing. Then, the complex was incubated in buffer alone, buffer containing 10 nM Fab-9 or 50 nM 52012. FIG. 3B: A similar experiment was performed to determine if 52012 could dissociate Fab-9 from purified IIb-IIIa.

DETAILED DESCRIPTION OF THE INVENTION

As used in the specification and in the claims, "a" can mean one or more, depending upon the context in which it is used.

As used herein, "ILD" refers to Integrin Ligand Dissociator, and indicates an antagonist compound causing the dissociation of a ligand which is already bound to its target integrin at a ligand binding site. In particular, an ILD can bind a second binding site on the integrin and thereby result in dissociation of the ligand from its ligand binding site on the integrin.

There is strong evidence that the physiologic binding site for IIb-IIIa within fibrinogen is an independent motif in the carboxyl terminus of fibrinogen gamma chain. This site is commonly referred to as the gamma chain motif, and it is not structurally related to RGD.

The present invention teaches that IIb-IIIa contains at least two ligand binding pockets and that these two sites are interacting (FIG. 2). Importantly, the present invention demonstrates that ligands which bind at an alternative binding site, such as Ligand Binding Site I, can enact the dissociation of ligand that is already pre-bound at Site II. Because of their unique ability to induce the dissociation of fibrinogen from IIb-IIIa, these antagonists are called Integrin-Ligand Dissociators. Furthermore, Integrin-Ligand Dissociators are shown to be capable of enacting the dissolution of pre-formed platelet aggregates. These findings indicate a novel approach toward anti-platelet therapy that is a strong departure from the current prophylactic strategy of applying antagonist prior to formation of vascular occlusions. Rather, the current information shows that Integrin-Ligand Dissociators, can be applied to reverse platelet aggregates that have already formed.

Thus, the present invention provides a method of dissociating a ligand bound to its integrin receptor at its ligand binding site, comprising administering to a ligand:receptor complex a molecule capable of binding the receptor at a second binding site and thereby dissociating the ligand from the receptor.

The present invention can be utilized with any integrin having at least two ligand binding pockets. Each integrin has an alpha and beta subunit and the subunits are usually named with a number designation (e.g., beta1), although in some cases the subunit is named with a letter which is derived from the historical name of the receptor. For example, the integrin can be a human integrin. The following is an exemplary list of the human integrins, along with examples of their known natural ligands:

αIIbβ3 is expressed on platelets and megakaryocytes. Examples of natural ligands for this integrin include, but are not limited to, fibrinogen, the derivative of fibrinogen called fibrin, von Willebrand factor, fibronectin, vitronectin and thrombospondin. αIIbβ3 also binds to many proteins that are present in snake venom called "disintegrins." αIIbβ3 also binds to the Lyme disease spirochete, *Borrelia burgdorferi*. (αIIbβ3 is also likely to bind to many other proteins containing the RGD sequence).

αvβ3 can be widely expressed, but is a clear drug target on osteoclasts, angiogenic endothelial cells and many tumor cells. Examples of natural ligands for αvβ3 include, but are not limited to, vitronectin, osteopontin, bone sialoprotein, fibronectin, von Willebrand factor, fibrinogen, fibrin, laminin, PECAM, thrombospondin, the penton base protein of adenovirus (nearly all serotypes), tenascin, matrix metalloproteinase II and the TAT protein of human immunodeficiency virus. (αvβ3 is also likely to bind to many other proteins containing the RGD sequence).

αvβ5 is widely expressed. It can be considered a drug target because it participates in angiogenesis by endothelial cells (angiogenesis is required for tumor growth). Examples of ligands for αvβ5 include, but are not limited to, vitronectin, osteopontin and the penton base protein of adenovirus( most serotypes) and the TAT protein of human immunodeficiency virus. αvβ5 is also expected to bind to other proteins which contain the RGD sequence.

αvβ1 is not well studied. Examples of its natural ligands include, but are not limited to, vitronectin, fibronectin and osteopontin. (αvβ1 is likely to bind other proteins containing RGD).

αvβ6 is expressed in the lung and in a few other tissues. Its natural ligands include vitronectin, fibronectin and tenascin. (αvβ6 is also likely to bind to other proteins which contain the RGD motif.)

αvβ8 is expressed in the kidney, brain, ovary and uterus. Its ligands are not known, although it will bind to RGD peptides and is believed to bind to natural proteins containing the RGD sequence.

α5β1 is widely expressed and is thought to be important in tumor progression. Its natural ligand is fibronectin. a5β1 is one of the integrins that can bind to the RGD motif.

α4β1 is expressed on cells of monocytic lineage, on endothelial cells and on some tumor cells. Its ligands are Vascular Cell Adhesion Molecule (VCAM) and fibronectin. α4β1 can also bind to the RGD motif.

α3β1 binds to laminin; particularly the laminin isoform called epiligrin.

α2β1 binds to collagen and to laminin. It also binds to echovirus and mediates the infection of cells by this virus.

α6β1 has the natural ligands collagen and laminin. It is also a constituent of structures called hemidesmosomes that link two cells together, so it may bind to proteins contained within hemidesmosomes.

α1β1 has collagen as its natural ligand.

α4β7 has VCAM, fibronectin and MadCAM as its natural ligands.

α6β4 has kalinin, merosin, and beta-4 laminin as its natural ligands.

αLβ2 is expressed on leukocytes (white blood cells). Its natural ligands include Intercellular Adhesion Molecule-1 (ICAM-1) and it also binds to ICAM-2 and ICAM-3.

αMβ2 is also expressed on leukocytes. Its natural ligands include ICAM-1, fibrinogen, factor X and iC3b.

αxβ2 is expressed on leukocytes. It has fibrinogen and iC3b as its natural ligands.

ILDs can comprise, for example, a protein, peptide, or organic molecule with a structure based on or resembling the arg-gly-asp sequence. Examples of such compounds include, but are not limited to, 1) a peptide comprising the sequence gly-arg-gly-asp-ser-pro (GRGDSP, SEQ ID NO:1), or any other peptide, cyclic or non-cyclic, containing the RGD motif; 2) a peptide derived from the carboxyl-terminus of fibrinogen gamma chain with an amino acid sequence: his-his-leu-gly-gly-ala-lys-gln-ala-gly-asp-val (HHLGGAKQAGDV, SEQ ID NO:2); 3) Fab-9, an RGD-containing Fab fragment of a human antibody that was created by phage display [2]; 4) a number of RGD-containing Fab-fragments that were generated from phage display libraries like the one containing Fab-9 [3]; 5) the protein called "Loop-Grafted tissue plasminogen activator LG-tPA, which was engineered to bind to platelet integrin αIIbβ3 (IIb-IIIa)[4]; and 6) any number of RGD mimetics that have been reported in the literature or used in human clinical trials including, but not limited to, integrilin, lamifiban, fradriban, lefradrifiban, abciximab, sidrafiban (Genentech), tirofiban (Merck), xemlofiban and orbofiban.

An ILD may also be comprised of peptides, or organic molecules with structures that are not related to RGD.

An ILD may be a monoclonal or polyclonal antibody that was generated by immunization with an integrin, or by immunization with a recombinant fragment of integrin, or by immunization with cells expressing an integrin. Such ILDs can include antibodies such as 1) the antibody 7E3 [5, 6], or abciximab, which is a recombinant derivative of antibody 7E3 that is a mouse-human chimera and is sold under the trade name ReoPro, and 2) the antibody LM 609, which binds to the αvβ3 integrin [7].

In the case of integrins which do not bind the arg-gly-asp (RGD) sequence, an ILD can also be comprised of a fragment, peptide, peptide mimetic, or organic molecule based upon the structure of one of its ligands. One such example can include an ICAM mimetic which could be applied to dissociate integrin αLβ2 from its ligands. Alternatively such an ILD can also include a peptide having the amino acid sequence EILDV (SEQ ID NO:3), or its derivatives and mimetics, which can be applied to dissociate ligands from the α4β1 integrin. Alternatively, an ILD can resemble a peptide with a sequence similar to the αMβ2 binding site within fibrinogen that could be applied to dissociate ligands from αMβ2.

Any molecule can be screened for effectiveness in dissociating any selected integrin from a selected ligand using standard techniques. For example, one can use Surface Plasmon Resonance (SPR), a cell-based screen or a ligand binding assay. These methods are described below.

Method 1. Screening for Integrin Ligand Dissociators Using Surface Plasmon Resonance (SPR).

In most cases, ligand binding to a protein can be described by two kinetic steps. The first is ligand association, which is described by the constant $k_1$ and the second is ligand dissociation, which is described by the constant $k_{-1}$. The affinity, or tightness of binding, between a ligand and its receptor is described by an overall affinity constant called $k_d$. By definition $k_d = k_{-1}/k_1$. The important distinction between ILDs and other integrin antagonists is that ILDs operate by increasing the rate of ligand dissociation ($k_{-1}$). The integrin antagonists that have been described to date are thought to function by decreasing the rate of ligand association ($k_1$). Hence, in screening for ILDs it is important to verify that the ILD increases the rate of ligand dissociation. This can be accomplished by any number of kinetic studies which involve purified proteins, or even whole cells.

In one embodiment, ILDs can be identified by the ability to increase the rate of dissociation between an integrin and its natural ligand, or a known mimic of its natural ligand, with Surface Plasmon Resonance (SPR), for example, using the BIACORE Surface Plasmon Resonance™ instrument. SPR is a technique that measures ligand association and dissociation in "real time." To screen for an ILD using plasmon resonance, the following steps would be taken:

1) The integrin is immobilized on the surface of the sensor chip;

2) The integrin is allowed to bind a natural ligand, or a known mimic of the natural ligand, by injecting that ligand into the instrument and allowing it to make contact with the receptor immobilized on the BIACORE Surface Plasmon Resonance™ sensor chip. The binding between ligand and integrin results in an increase in the mass of the protein complex bound to the sensor chip, which is detected and reported as a change in plasmon resonance. This is reported as an increase in Response Units (or RU);

3) The rate of dissociation of the natural ligand is measured by changing the buffer of the mobile phase so that it lacks any free natural ligand. This change halts the binding reaction and allows the bound ligand to begin dissociating at its native rate. This natural dissociation rate must be recorded; and 4) The candidate ILD, or a fluid containing a potential ILD, is introduced into the flow cell containing the integrin-:ligand complex. Then, the rate of ligand dissociation is measured in the presence of the candidate ILD.

Any compound or substance that increases the rate of dissociation between an integrin and its ligand is considered to be an ILD.

It is important to note that the configuration of the assay could take several different forms. For example, rather than immobilizing the integrin on the sensor chip, one could immobilize the ligand. In such case, the integrin would be allowed to bind the immobilized ligand prior to measuring dissociation rates.

The use of plasmon resonance is just one approach toward screening for ILDs, as any method of quantifying ligand dissociation rate in the presence and absence of an ILD would suffice. Such methods can include, but are not limited to, stopped flow kinetics, whole cell-based radioligand binding assays, microcalorimetry, fluorimetry, etc., as would be well known in the art.

Method 2: A cell-based Screen for ILDs.

Integrins mediate the adhesion of cells to matrix proteins and to other cells. Thus, one desirable property of an ILD is that it be able to reverse cell adhesion. Thus, one method of screening for ILDs is to examine the ability to release cells from an adherent surface. In one example, this can be accomplished by coating optically active beads with an integrin ligand. The beads, which form a relatively monodisperse solution, are then mixed with cells which express the target integrin. As the integrin binds to its ligand, the cells adhere to the ligand-coated beads and cause them to agglutinate. Such agglutination results in a clearance of the solution and a decrease in its optical density. Such a decrease is conveniently measured by any spectrophotometer. Candidate ILDs are introduced into the solution of agglutinated beads. Any compound that dissociates the integrin from its ligand (an ILD) will reverse cell adhesion to the ligand-coated beads and reduce agglutination of the beads. Such reduction in agglutination results in an increase in optical density of the solution.

This method has the advantage that it can identify ILDs that operate via any number of potential biochemical mechanisms. For example, an ILD could function by interrupting an important cellular signaling cascade that is required to maintain a tight binding affinity between an integrin and its ligand. Thus, an ILD that antagonizes such a signaling cascade would increase the rate of dissociation between an integrin and its ligand, but by a mechanism that is different from binding directly to integrin.

A general method for using a cell-based assay for screening for ILDs is as follows:

1) Coat optically active small diameter polystyrene beads with an integrin ligand, or a ligand mimic. Record the optical density of the suspension of beads at an appropriate wavelength of light. It is expected that in many cases a measure of the turbidity of the solution will suffice;

2) In solution, add cells expressing a given integrin to a suspension of ligand-coated beads. Allow the cells and beads to bind to one another for a time sufficient to cause agglutination of the beads and a reduction in the optical density of the solution. Measure and record the optical density of the solution;

3) Add a small volume of a solution containing a candidate ILD, or any combination of candidate ILDs, or any series of molecules that may act in concert as ILDs, to the agglutinated beads. Generally, the sample should be gently mixed to facilitate the diffusion of the candidate ILD into the sample. Allow a sufficient period of time for the ILD to dissociate integrin from its ligand.; and 4) Measure the optical density (or turbidity) of the solution and compare it to the optical densities recorded in steps 1 and 2. Any candidate molecule that increases the optical density of the solution over that recorded following step 2 is considered an ILD. For example, a "good" ILD might be able to completely reverse the adhesion of cells to the ligand coated beads. In this case, the optical density of the solution would return to that recorded following step 1.

It should be emphasized that this is only one approach toward using a cell-based assay for screening for ILD's. A number of different strategies for measuring cell adhesion to integrin ligands are known in the art which could easily be adapted to screen for ILDs.

Method 3. A Purified Integrin Ligand Binding Assay Adapted to Screen for ILDs.

Many integrins bind to their ligands such that the two molecules do not dissociate rapidly in the presence of buffer or saline. This allows screening for ILDs by simply comparing the amount of integrin ligand complex remaining after an exposure to a candidate ILD for a sufficient period of time. This type of screen is readily performed using purified integrins and their ligands. In most cases, the strategy will function best when the ligands are labeled with radioiodine or with an alternative labeling approach like biotinylation such that the bound ligand can be detected and quantified. A general method for such a screen is adapted from methods previously described methods for examining ligand association with integrins [1]. The adaptation is as follows:

1) Immobilize a purified integrin on a solid support, such as a plastic microtiter plate;

2) Allow a labeled ligand to bind to the immobilized integrin;

3) Wash the microtiter wells containing the integrin and ligand to remove any "free" or unbound ligand;

4) Detect and record the amount of ligand bound;

5) Add either buffer (saline) or buffer solution containing a candidate ILD to the microtiter well containing the complex between integrin and its ligand. Allow sufficient period of time for dissociation to occur; and 6) Measure the amount of ligand remaining bound to integrin in samples in which buffer alone was added and in samples in which candidate ILDs were added. Any sample in which the amount of ligand remaining bound is lower than that remaining bound in the samples exposed to buffer is an ILD.

The present invention provides several methods of dissociating a ligand from its integrin receptor, which dissociation has a therapeutic effect. Thus, the present invention includes a method of dissociating a platelet integrin from a ligand and thereby enacting the dissolution of a platelet thrombus in, for example, a subject with unstable angina, stroke, atherosclerosis, or acute myocardial infarction, comprising administering to the subject an ILD, thereby enacting the dissolution of the platelet thrombus in the subject. An effective amount would be administered, such effective amount being a platelet thrombus dissolving amount. The platelet integrin can be platelet integrin $\alpha II\beta 3$, wherein the dissociation renders the platelet-rich thrombus more susceptible to digestion with thrombolytic agents such as tissue plasminogen activator in patients with thrombotic conditions like acute myocardial infarction and stroke.

The subjects of the present invention can include, but are not limited to, humans, dogs, cats, cows, horses, pigs and other valuable and economically important animals and birds.

The present invention also provides a method of enacting de-adhesion of osteoclasts from the bone surface to halt bone loss in a patient with osteoporosis, comprising administering to the patient an ILD capable of binding $\alpha v\beta 3$ and dissociating ligands previously bound to $\alpha v\beta 3$, thereby dissociating the $\alpha v\beta 3$ integrin from its ligands and enacting the de-adhesion of osteoclasts from the bone surface to halt bone loss in the patient. An effective amount would be administered, such effective amount being an osteoclast de-adhesion amount.

The present invention also provides a method of enacting the de-adhesion of angiogenic endothelial cells in a patient with a pathologic condition associated with angiogenesis, such as cancer, diabetic retinopathy, or psoriasis, comprising administering to the patient an ILD capable of binding $\alpha v\beta 3$ and/or $\alpha v\beta 5$ and capable of dissociating ligands previously bound to $\alpha v\beta 3$ and/or $\alpha v\beta 5$, thereby dissociating the $\alpha v\beta 3$ and/or $\alpha v\beta 5$ integrins from their ligands and enacting the de-adhesion of angiogenic endothelial cells in the patient. An effective amount would be administered, such effective amount being an endothelial cell de-adhesion amount.

The present invention also provides a method of inducing the dissociation of matrix metalloproteinase-2, or any other matrix metalloproteinase from the $\alpha v\beta 3$ integrin to halt or reverse the invasion of angiogenic endothelial cells into a tumor, or to halt tumor cell invasion in a patient with cancer, comprising administering to the patient an ILD capable of binding $\alpha v\beta 3$ and capable of dissociating ligands previously bound to $\alpha v\beta 3$, thereby inducing the dissociation of matrix metalloproteinase-2, or any other matrix metalloproteinase from the $\alpha v\beta 3$ integrin to halt or reverse the invasion of angiogenic endothelial cells into a tumor, or to halt tumor cell invasion in the patient. An effective amount would be administered, such effective amount being a matrix metalloproteinase dissociating amount.

The present invention also provides a method of inducing dissociation of a ligand from the $\alpha v\beta 3$ integrin to reverse intimal thickening and vascular smooth muscle cell proliferation in a patient with atherosclerosis or a patient that has developed complications following vascular procedures like balloon angioplasty, comprising administering to the patient an ILD capable of binding $\alpha v\beta 3$ and capable of dissociating ligands previously bound to $\alpha v\beta 3$, thereby inducing dissociation of a ligand from the $\alpha v\beta 3$ integrin to reverse intimal thickening and vascular smooth muscle cell proliferation in the patient. An effective amount would be administered, such effective amount being a $\alpha v\beta 3$ integrin ligand dissociating amount.

The present invention also provides a method of enacting the dissociation of any of the ligands from the $\beta 2$-integrins ($\alpha L\beta 2$, $\alpha M\beta 2$, $\alpha x\beta 2$) to enact the dissociation of one or more of these integrin from their ligands in patients with inflammatory conditions like arthritis, inflammatory bowel disease, or in a patient that has had an organ transplant and is rejecting the donated organ, comprising administering to the patient an ILD capable of binding one or more β2-integrin and capable of dissociating ligands previously bound to one or more β2-integrin, thereby enacting the dissociation of any of the ligands from the β2-integrins and treating inflammatory conditions like arthritis, inflammatory bowel disease or reducing organ rejection in the patient. An effective amount would be administered, such effective amount being a β2-integrin ligand dissociating amount.

The present invention also provides a method of enacting the dissociation of the α4β1 integrin from its ligands to reverse the adhesion of neutrophils at atherosclerotic plaques in a patient with atherosclerosis, comprising administering to the patient an ILD capable of binding α4β1 and capable of dissociating ligands previously bound to α4β1, thereby reversing the adhesion of neutrophils at atherosclerotic plaques and treating atherosclerosis in the patient. An effective amount would be administered, such effective amount being a α4β1 ligand dissociating amount.

The present invention also provides a method of enacting the dissociation of the α4β1 integrin from its ligands to cause the dissociation of neutrophils and/or eosinophils from sites of adhesion in a patient with asthma, comprising administering to the patient an ILD capable of binding α4β1 and capable of dissociating ligands previously bound to α4β1, thereby reducing or inhibiting asthmatic reaction in the patient. An effective amount would be administered, such effective amount being a neutrophil and/or eosinophil dissociating amount.

The present invention also provides a method of enacting the dissociation of an integrin on a target cell from its ligand, causing cellular de-adhesion and the subsequent programmed cell death of the target cell, comprising administering to the target cell an ILD capable of binding the integrin and capable of dissociating ligands previously bound to the integrin, thereby enacting the dissociation of an integrin from its ligand and causing cellular de-adhesion and the subsequent programmed cell death of the target cell. An effective amount would be administered, such effective amount being a integrin: ligand dissociating amount.

Effective amounts can be readily determined by standard methods. In general, however, these dosages can approximate dosages of compounds administered for the prevention of the same condition to be treated. These dosages will be well known to the skilled artisan (9–12). Dosages can be optimized based on the size of the subject and the extent of the condition or disease to be alleviated by the administration of the compound.

Compounds can be administered to a subject or an animal model by any of many standard means for administering the particular compound. For example, compounds can be administered orally, parenterally (e.g., intravenously), by intramuscular injection, by intraperitoneal injection, topically, transdermally, or the like. Compounds can be administered, e.g., as a complex with cationic liposomes, or encapsulated in anionic liposomes. Compositions can include various amounts of the selected compound in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Actual methods of preparing such dosage forms are known, or will be apparent, to those skilled in this art (13).

The compositions of this invention can include, as noted above, an effective amount of the selected compound in combination with a pharmaceutically acceptable carrier and, in addition, can include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

The present invention is more particularly described in the following examples which are intended as illustrative only since numerous modifications and variations therein will be apparent to those skilled in the art.

EXAMPLES

Evidence that GPIIb-IIIa Contains Two Interacting Ligand Binding Sites.

IIb-IIIa can bind to two types of ligands, one of which is RGD and the other being a motif in the carboxyl-terminus of the fibrinogen gamma chain which lacks structural similarity to RGD. The binding of IIb-IIIa to the sequence in the carboxyl-terminus of fibrinogen is necessary for platelet aggregation and is of clear physiologic relevance. Prior work using small peptide ligands based on the RGD and gamma chain motifs led to the current notion that the two types of ligands bind to an overlapping binding pocket in a mutually exclusive manner.

The present studies challenge the idea that IIb-IIIa contains a single ligand binding pocket. These studies indicate that IIb-IIIa contains two separate, but interacting ligand binding pockets.

Much of the present data makes use of three ligands. Fibrinogen, the physiologic ligand for IIb-IIIa; Fab-9, which is an RGD-containing antibody that we engineered to bind IIb-IIIa using phage display and which is considered to be an RGD mimic; and 52012 (another RGD mimetic).

Figure 1A:
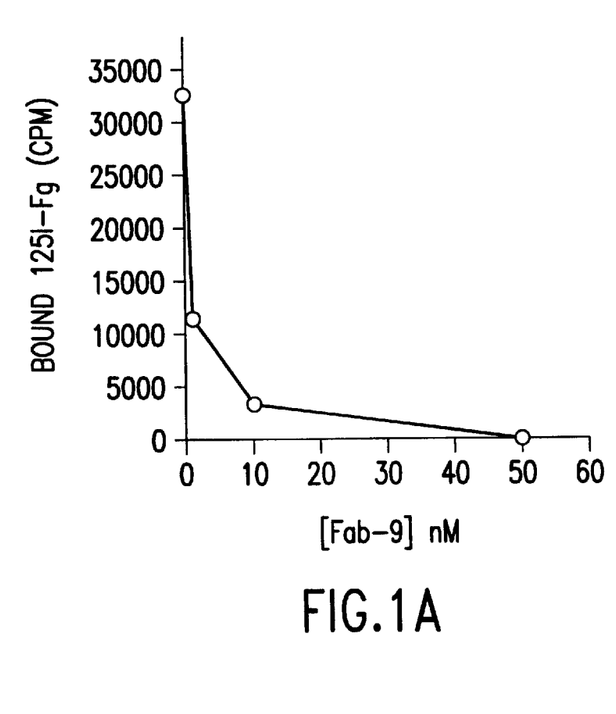
FIGS. 1A and 1B. Fibrinogen and Fab-9 bind distinct sites on IIb-IIIa. Studies were conducted with purified IIb-IIIa to determine whether Fab-9 (an RGD mimic) and fibrinogen bind to the same site on the integrin. IIb-IIIa was immobilized in microtiter plates and was allowed to bind either $^{125}$I-fibrinogen (FIG. 1A) or to $^{125}$I-Fab-9 (FIG. 1B). The binding of $^{125}$I-fibrinogen was challenged with unlabeled Fab-9. Similarly, the binding of $^{125}$I-Fab-9 was challenged with unlabeled fibrinogen. Although Fab-9 blocks the binding of fibrinogen (FIG. 1A), fibrinogen does not interfere with the binding of Fab-9 (FIG. 1B)
Figure 1B:
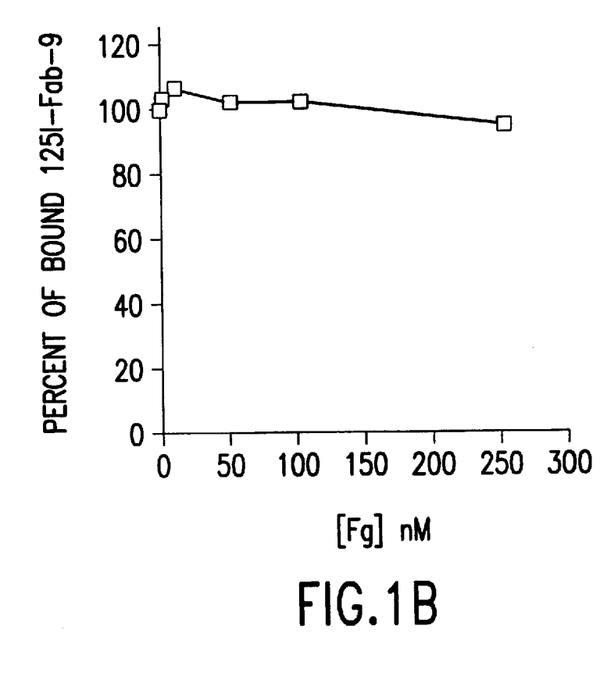

To determine if fibrinogen and Fab-9 actually bind the same site on IIb-IIIa, a series of competition binding studies were carried out. The ability of the two ligands to compete for binding to IIB-IIIa was measured. Fab-9 blocked the binding of fibrinogen to IIB-IIIa (FIG. 1A). However, fibrinogen failed to block the binding of Fab-9 to the integrin (FIG. 1B). These data prove that the two proteins bind to different sites on the integrin. These sites are designated as Site I, which binds to Fab-9 and Site II, which interacts with fibrinogen (FIG. 2).

Figure 3A:
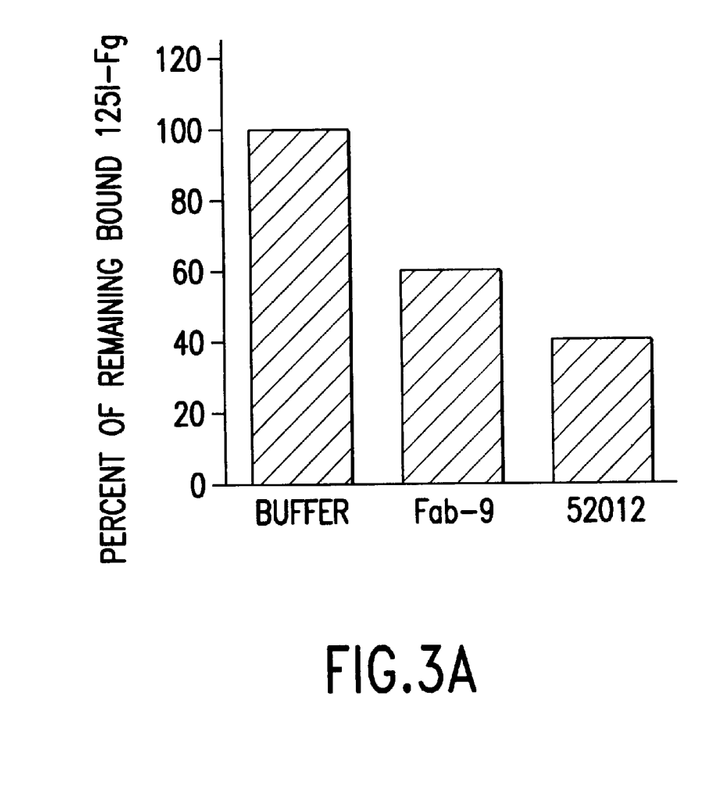
Figure 3B:
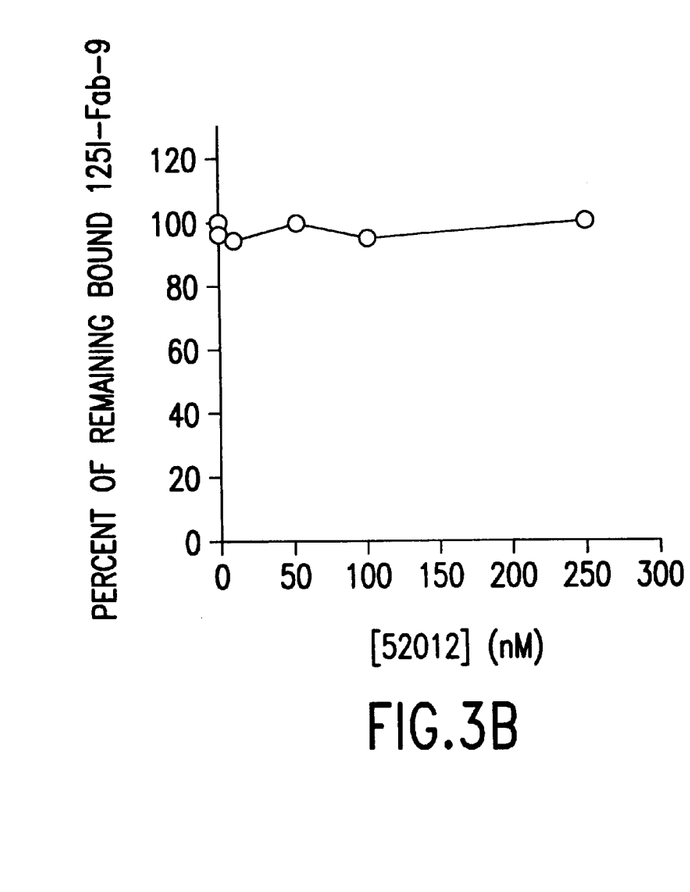

Based on this finding, it was hypothesized that IIB-IIIa contains two ligand binding sites and that one site regulates the affinity of ligand for the other site. To test this "interacting site" hypothesis, the effects of Fab-9 and 52012 on the dissociation of pre-bound fibrinogen were examined. By definition, ligands that bind a common site on a receptor have no ability to influence the dissociation rate of bound ligand because they cannot bind to the occupied site. In contrast, ligands which bind to separate, or allosteric, sites can regulate the affinity for ligands at the second site. Both RGD-type ligands, Fab-9 and 52012, promoted the dissociation of between 50 and 60% of the bound fibrinogen within a three hour time period (FIG. 3A). As is well known, fibrinogen does not dissociate from purified IIB-IIIa in the presence of buffer. Interestingly, 52012 failed to increase the dissociation of Fab-9 from purified IIB-IIIa (FIG. 3B). The simplest interpretation of these observations is that both RGD-mimic ligands, Fab-9 and 52012, bind to a common site on IIB-IIIa (Site I) and that this site regulates the rate of dissociation of fibrinogen from Site II.

Figure 4A:
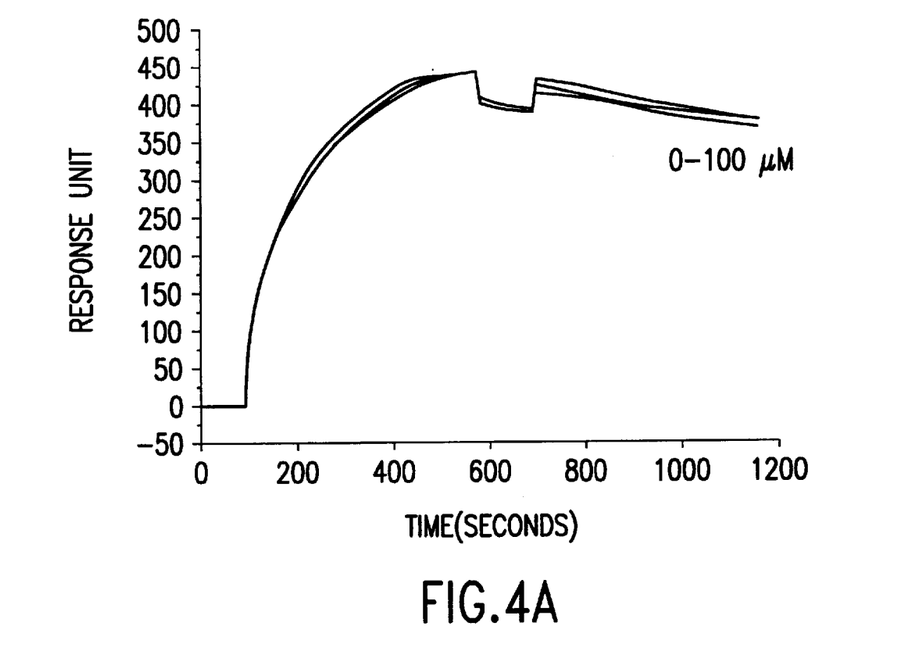
FIGS. 4A and 4B. Measuring the ability of 52012 to dissociate fibrinogen and Fab-9 from IIb-IIIa in real time. Studies were performed with Surface Plasmon Resonance to examine the ability of 52012 to induce the dissociation of ligands from IIb-IIIa. Fab-9 (FIG. 4A) or fibrinogen (FIG. 4B) were immobilized on the sensor chip and then allowed to bind to purified IIb-IIIa. At a specific time, 52012 was introduced by injection into the flow cell.
Figure 4B:
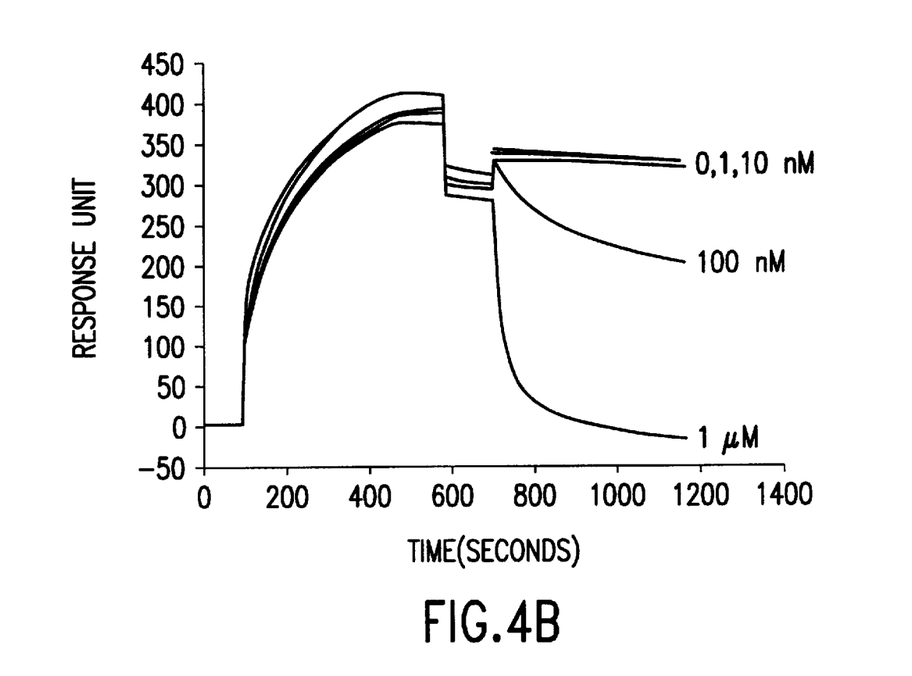

To verify the effect of RGD-type ligands on the dissociation of fibrinogen from IIB-IIIa, dissociation rates were measured in real time using Surface Plasmon Resonance (SPR). As shown in FIG. 4B, 52012 was able to induce the dissociation of fibrinogen from IIB-IIIa, increasing the off-rate by twenty-fold (from $6 \times 10^{-5} s^{-1}$ to $1 \times 10^{-2} s^{-1}$) However 52012 did not affect the dissociation of Fab-9 from IIB-IIIa (FIG. 4A), a finding consistent with the result shown in FIG. 3B and also consistent with the idea that 52012 and Fab-9 bind to the same site. It is also of note that the concentration of 52012 required to induce dissociation of fibrinogen was virtually identical to that required to prevent association of fibrinogen. This observation indicates that fibrinogen binding to Site II has little effect on the binding affinity of 52012 at Site I. Hence, binding of ligands like 52012 and Fab-9 to Site I can regulate both aspects of fibrinogen binding affinity ($k_1$ and $k_{-1}$), but that fibrinogen does not influence the affinity for ligands at Site I.

Figure 5:
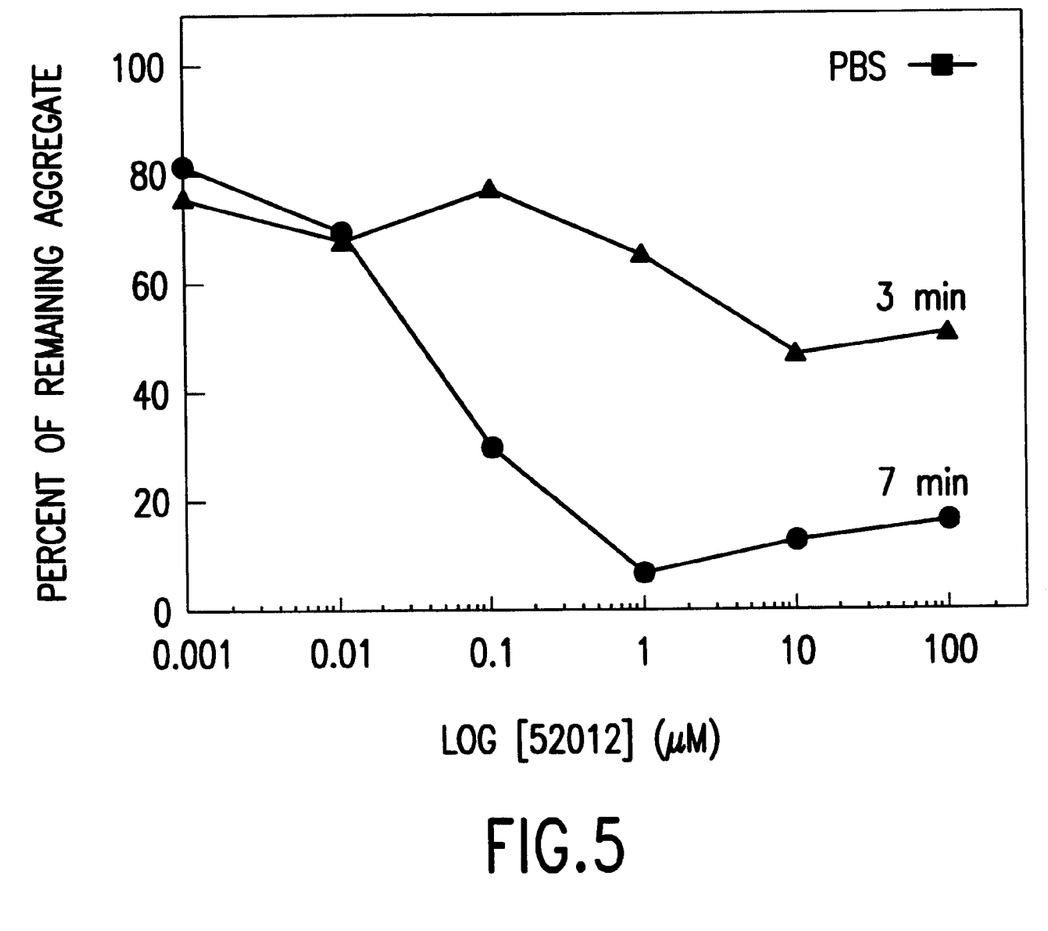
FIG. 5. 52012 can dissociate a pre-formed platelet aggregate. Platelet-rich plasma was incubated with fibrinogen coated blue beads which absorb light at 650 nM. Upon addition of ADP as agonist, the platelets aggregate along with the blue beads, causing the optical density to change. This system was used to measure the effect of 52012 on pre-formed platelet aggregates. Aggregates were allowed to form for 10 min. following addition of ADP. 52012 was added at the given concentrations. The dissolution of the aggregate was followed as a function of time and was largely complete within 7 minutes.

One implication of the two site interacting model is that the binding of ligand (or drug) to Site I on IIB-IIIa may dissociate a platelet thrombus. Therefore, studies were conducted in which a platelet aggregate was formed in the presence of optically active fibrinogen-coated blue beads. The blue beads act as a tracer as their clearance from the solution during platelet aggregation reports the extent of aggregation. When RGD mimics 52012 or Fab-9 were added to platelets prior to platelet stimulation, aggregation was prevented. More significantly, both RGD-like ligands could induce the dissociation of a pre-formed platelet thrombus (FIG. 5), a result that is consistent with their ability to induce the dissociation of fibrinogen from IIB-IIIa (FIGS. 1 and 3).

These data reveal a previously unappreciated kinetic interplay between two separate ligand binding sites on IIB-IIIa. The study indicates that two ligand binding sites are distinct and non-overlapping. Binding Site I interacts with Fab-9 and other RGD mimics. Binding Site II binds to fibrinogen. The two ligand binding sites are linked in a unique manner. The binding of fibrinogen at Site II has no effect on the binding affinity for RGD-type ligands at Site I. In contrast, the binding of RGD-type ligands to Site I regulates both the association rate and, more importantly, the dissociation rate of fibrinogen at Site II. A model of the two interacting ligand binding pockets on IIB-IIIa is shown in FIG. 2.

These results have several implications. First, the findings support a new therapeutic strategy for interfering with the function of IIB-IIIa. Prior understanding of the binding sites on IIB-IIIa indicated that the receptor interacted with two classes of ligands in a "mutually exclusive" manner. With this mechanism of binding, antagonists of the integrin could only operate by preventing the association of fibrinogen with the integrin. Hence, drugs would only be effective when applied prior to the formation of a thrombus. The results presented here demonstrate that the binding of RGD-type ligands/antagonists to IIB-IIIa can assist in dissociating existing thrombi. Clearly the dissolution of a thrombus is complex and involves many additional factors, but the current findings support the interaction of small molecules with these sites as means of dissociating existing thrombi.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES (1) Smith, J. W., R. S. Piotrowicz, and D. M. Mathis, A mechanism for divalent cation regulation of β3-integrins. *Journal of Biological Chemistry*, 1994. 269:960–967.
(2) Barbas, C. F., L. Languino, and J. W. Smith, High-affinity self-reactive human antibodies by design and selection: targeting the integrin ligand binding site. *Proceedings of the National Academy of Sciences* (USA), 1993. 90:10003–10007.
(3) Smith, J. W., et al., Building synthetic antibodies as adhesive ligands for integrins. *Journal of Biological Chemistry*, 1994. 269:32788–32795.
(4) Smith, J. W., K. Tachias, and E. L. Madison, Protein Loop Grafting to Construct a Variant of Tissue Type Plasminogen Activator that Binds Platelet Integrin αIIbβ3. *Journal of Biological Chemistry*, 1995. 270(51):30486–30490.
(5) Coller, B. S., A new murine monoclonal antibody reports an activation-dependent change in the conformation and/or microenvironment of the platelet glycoprotein IIB-IIIa complex. *J.Clin.Invest.*, 1985. 76:101.
(6) Coller, B. S., K. Anderson, and H. F. Weisman, New antiplatelet agents: platelet GPIIb/IIIa antagonists. *Thromb. Haemost.*, 1995. 74(1):302–8.
(7) Cheresh, D. A. and R. C. Spiro, Biosynthetic and functional properties of an Arg-Gly-Asp- directed receptor involved in human melanoma cell attachment to vitronectin, fibrinogen, and von Willebrand Factor. *Journal of Biological Chemistry*, 1987. 262:17703–17711.
(8) Zablocki, J. A., et al. *Journal of Medicinal Chemistry*, 1993. 36:1811–1819.
(9) Mousa, S. A., et al. *Stroke*, 1997. 28:830–836.
(10) Kaida, T., et al. *Thrombosis and Haemostasis*, 1997. 77(3):562–567.
(11) Cook, J. J., et al. *J. Pharmacol. Exp. Ther.*, 1997. 281(2):677–689.
(12) Frishman et al. *Am. Heart J.*, 1995. 130:877–892.
(13) *Remington's Pharmaceutical Sciences*, current edition. E. W. Martin, (ed.), Mack Publishing Co., Easton, Pa., U.S.A.

What is claimed is:

1. A method of disaggregating an existing platelet thrombus in a blood vessel in a subject, comprising administering to the subject a compound which dissociates fibrinogen bound to a first site on platelet glycoprotein IIb-IIIa, by binding a second interacting site on platelet glycoprotein IIb-IIIa, thereby disaggregating the platelet thrombus.

2. The method of claim 1, wherein the existing platelet thrombus forms an occlusion of a blood vessel.

3. The method of claim 1, wherein the compound is an Arg-Gly-Asp (RGD) mimetic.

4. The method of claim 1, wherein the compound is the engineered human Fab fragment called Fab-9.

5. The method of claim 1, wherein the compound is a peptide with sequence Gly-Arg-Gly-Asp-Ser-Pro (SEQ ID NO:1).

6. The method of claim 1, wherein the compound is a peptide with a sequence based on the carboxyl-terminus of the fibrinogen-gamma chain.

7. The method of claim 6, wherein the peptide has the sequence His-His-Leu-Gly-Gly-Ala-Lys-Gln-Ala-Gly-Asp-Val (SEQ ID NO:2).

8. The method of claim 1, wherein the subject is a human.

9. The method of claim 1, wherein the subject has a condition selected from the group consisting of unstable angina, stroke and myocardial infarction.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Gly Arg Gly Asp Ser Pro
 1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

His His Leu Gly Gly Ala Lys Gln Ala Gly Asp Val
 1               5                  10

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Glu Ile Leu Asp Val
 1               5
```